United States Patent
Yee et al.

(10) Patent No.: US 7,989,217 B2
(45) Date of Patent: Aug. 2, 2011

(54) METHOD FOR DETERMINING HCG LEVELS IN FLUID SAMPLES

(75) Inventors: Hsiao-Ching Yee, Mill Creek, WA (US); Kuo-Ching Yee, Mill Creek, WA (US); Hsian-Pei Yee, Mill Creek, WA (US)

(73) Assignee: AmeriTek USA, Inc., Everett, WA (US)

( * ) Notice: Subject to any disclaimer, the term of this patent is extended or adjusted under 35 U.S.C. 154(b) by 497 days.

(21) Appl. No.: 11/693,638

(22) Filed: Mar. 29, 2007

(65) Prior Publication Data

US 2008/0241958 A1 Oct. 2, 2008

(51) Int. Cl.
*G01N 33/53* (2006.01)

(52) U.S. Cl. ......... 436/514; 435/7.1; 435/7.2; 435/7.93; 435/7.94; 435/7.5; 435/287.1; 435/287.2; 435/287.9; 435/805; 435/969; 435/970; 435/973; 436/518; 436/531; 436/533; 436/808

(58) Field of Classification Search .................. 435/7.1, 435/7.2, 7.93, 7.94, 7.5, 287.1, 287.2, 287.9, 435/805, 820, 969, 970, 973; 436/514, 518, 436/531, 533, 805, 808
See application file for complete search history.

(56) References Cited

U.S. PATENT DOCUMENTS 7,326,578 B2 * 2/2008 Bateman et al. .............. 436/514

FOREIGN PATENT DOCUMENTS

WO    WO 88/08534    * 11/1988

* cited by examiner

*Primary Examiner* — Bao Thuy L Nguyen
(74) *Attorney, Agent, or Firm* — Venture Pacific Law, PC

(57) ABSTRACT

The subject invention is an immunoassay for the semi-quantitative test kit for determination of human chrionic gonadtropin (hCG) in fluid sample (such as urine) as an aid in the diagnosis of a certain stage of pregnancy. The test device includes five strips having each having a dipping end or sample ends where sample can be applied. Results are indicated by coloration of two bands across a clear area of the strips, one band being coated with a reagent such as hCG antigens and the other with a reagent such as goat/rabbit polyclonal antibody gold conjugate. The combination of color indications on the bands provides the test results.

17 Claims, 3 Drawing Sheets

METHOD FOR DETERMINING HCG LEVELS IN FLUID SAMPLES

FIELD OF INVENTION

The present invention relates to techniques for determining whether a human has a particular disease, condition, illness or affliction, and more particularly to methods and apparatuses for determining human chorionic gonadotropin (hCG) levels.

BACKGROUND OF THE INVENTION

The hormone, human chorionic gonadotropin, hCG is produced during pregnancy. It is made by cells that form the placenta which nourishes the egg after it has been fertilized and becomes attached to the uterine wall. The hCG can be first detected by a normal blood test about 11 days after conception or about 12-14 days after conception with a urine test. In general the hCG level will double every 72 hours. The hCG level will reach its peak in 8 to 11 weeks of the pregnancy and then will decline and level off for the remainder of the pregnancy.

Table 1 shows the Gestational age of the nourished egg after LMP as being proportional to levels of hCG in blood or urine.

TABLE 1

| hCG level of Urine | Gestational age after LMP |
| --- | --- |
| <5.0 mIU/ml | Non pregnancy |
| 5-50 mIU/ml | 3 weeks |
| 5-426 mIU/ml | 4 weeks |
| 18-7,340 mIU/ml | 5 weeks |
| 1,080-56,500 mIU/ml | 6 weeks |
| 7,650-229,000 mIU/ml | 7-8 weeks |
| 25,700-288,000 mIU/ml | 9-12 weeks |
| 13,300-254,000 mIU/ml | 13-16 weeks |
| 4,060-165,400 mIU/ml | 17-24 weeks |
| 3,640-117,000 mIU/ml | 25-40 weeks |

Accordingly, the levels of hCG detected can be used as an aid to determine a fetus's gestational age and status at various stages of a pregnancy. For examples, a low hCG level could indicate possible miscarriage, blighted ovum, or ectopic pregnancy. A high level of hCG may indicate molar or multiple pregnancy.

There are many brands of pregnancy test kits commercially available, however they only provide a single answer (Yes or No) as to whether a specific level of hCG is reached. No additional information is provided regarding the various concentration levels of the hCG being detected. Clinician often use hCG level information in order to monitor the course of pregnancy, however currently there is a lack of convenient, inexpensive, point care technology and product available.

For example, in order determine the levels of hCG, one must be subjected to a standard lab test which utilizes ELISA hCG test by using a women's blood specimen. Although the results do show acute concentration of hCG as mIU/ml in blood, the procedure is involved and requires an invasive blood specimen collection procedure. To obtain the hCG concentration results, the blood is often transferred to a specialized laboratory where a laboratory technician performs the necessary tests. The laboratory is typically away from the clinic where women's blood specimen was taken. The ELISA hCG test takes about an hour to perform the test but there is the additional time for the hCG test results to be delivered back to a physician's clinic. Accordingly, to receive the results of a hCG test, there is usually a minimum one day turnaround. Another drawback is the cost of performing the hCG test at the specialized laboratory which requires additional labor and materials.

Gestational age can also be determined using a transvaginal ultrasound examination. The ultrasound examination enables a clinician to visualize at least a gestational sac once the hCG levels have reached between 1,000-2,000 mIU/ml which is in about 5 weeks into a pregnancy. However, ultrasound technology cannot detect the status of early stages of pregnancy which is an essential time to watch for possible health or abnormal courses of pregnancy.

There is a commercial test available for detecting hCG levels of 2000 mIU/ml or greater. The test is a Wampole immunochemical latex agglutination slide test. Clinicians utilize this product to monitor a large fluctuation in hCG levels in pregnant women after a miscarriage or a procedure when the hCG levels are supposed to drop substantially. Accordingly, there is much variation in the sensitivity of the Wampole slide test. Moreover, the latex agglutination process of the Wampole slide—based on latex agglutination process, its sensitivity can vary from 1000 mIU/ml or 3000 mIU/ml. Since the Wampole slide test is for detecting high hCG levels, it only provides a single level of hCG with no semi-quantitative information. In view of the shortcomings of current tests for hCG levels, there is a need for a simple to use, less evasive, inexpensive, accurate, hCG level tester that overcomes the disadvantages of current practices.

SUMMARY OF THE INVENTION

The subject invention is a test which enables rapid detection of various concentration levels of human chorionic gonadotropin (hCG) in a fluid sample, where the fluid sample can be urine or blood. The test is based on antibody function. A test kit has multiple strips having multiple strips assembled in a cassette. The cassette includes a backing sub-strip, an absorbent materials sub-strip, a cover sub-strip having a clear portion or window and a portion of antibody gold conjugate. The sub-strips are laminated with a short portion of the absorbent materials exposed at the dipping end. The window may have a T and a C on its inner side indicating the locations of the test band and control band respectively.

A test band is coated with a hCG antibody or a hCG antigen. A control band is coated with reagents such as goat/rabbit polyclonal antibodies as control capture antibodies. The antibody gold conjugate binds to the antigens or the antibody of the test band. In a test, a urine sample is applied, the urine sample migrates through the absorbent material, past the antibody gold conjugate portion and the bands. There are two different technology involved when detecting hCG concentration levels 25 mIU/ml, 100 mIU/mla or 500 mIU/ml and detecting hCG concentration levels 2,000 mIU/ml and 10,000 mIU/ml. At first three levels of hCG, the pre-developed respective test lines are made with invisible hCG antibodies, when the hCG concentration in the sample is more than 25 mIU/ml, 100 mIU/ml or 500 mIU/ml (the low hCG range), antibody gold conjugate binds with hCG antigen forming antibody-antigen complex, which are captured by the other antibody at the respective test lines at the respective window to display visible test line(s). For detecting 2000 mIU/ml and 10,000 mIU/ml, the respective test lines are sprayed of hCG antigens. At levels of 2,000 mIU/ml and 10,000 mIU/ml (the high hCG range), when the hCG concentration in the sample is more than 2,000 mIU/ml and 10,000 mIU/ml respectively, most of the antibody gold conjugate binds the hCG antigen in specimen before reaches the respective test line, and the already bound antibody gold conjugate can not further bind with the hCG antigen at the test line, thus passes through the test line without producing a visible test line respectively. If there is not sufficient hCG-antigen in the sample, then the un-bound antibody gold conjugate will bind to the hCG antigen on the test line, and produce a visible test line. When the hCG antigen level in sample is between 2000 mIU/ml and 10,000 mIU/ml, the test line for 2000 mIU/ml is invisible and 10,000 mIU/ml is visible. The control lines become visible in when antibody gold conjugate (hCG bound or un-bound) reaches the control line area. Visible control lines are to indicate that the procedure, reagents and test materials are likely to be functioning correctly.

Other aspects and advantages of the present invention will become apparent to those skilled in the art from reading the following detailed description when taken in conjunction with the accompanying drawings.

DETAILED DESCRIPTION OF THE INVENTION

Figure 1:
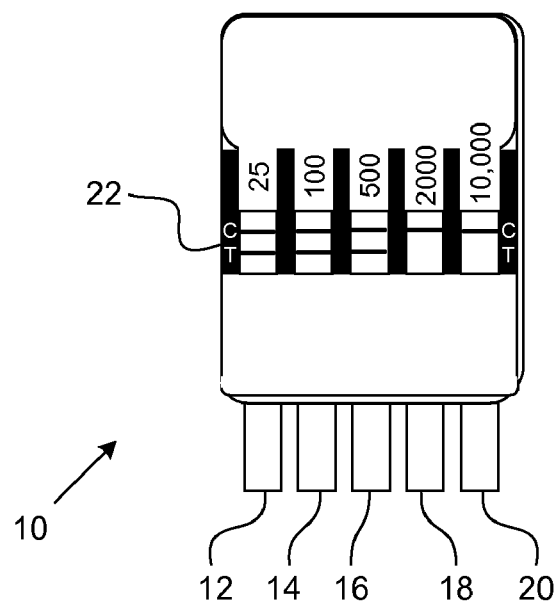
FIG. 1 illustrates a cassette enclosing five dip strips in accordance to an embodiment of the present invention.

The present invention is a test which enables rapid detection of various concentration levels of human chorionic gonadotropin (hCG) in a fluid sample and is based on antibody function. The fluid sample can be of many types including blood and urine. In accordance to an embodiment, multiple test strips are used to detect the various hCG levels. Each test strip has multiple result zones including a test area and a control area. The test areas on some test strips are coated with hCG antibody, while other test strips are coated with hCG antigen. The control area on the test strip is coated with reagents such that it would capture the conjugated color particles.

In a hCG test, a fluid sample is applied to the test strip by dipping the strip into the fluid sample which migrates through absorbent material of the test strip passes the antibody gold conjugate portion and the result zones coated with anti-body or antigen material. Among the five test strips, there are mainly two different biological/chemical reactions involved: the first when detecting 25 mIU/ml, 100 mIU/ml and 500 mIU/ml; and the second when detecting 2,000 mIU/ml and 10,000 mIU/ml. At the three lower levels of hCG, when the hCG concentration in the sample is more than 25 mIU/ml, 100 mIU/ml, or 500 mIU, antibody gold conjugate binds to hCG antigens (forming antibody-antigen complex) in the fluid sample which is captured by antibody in the test line and causing the test area to become visible.

When the hCG concentration in the sample is more than 2,000 mIU/ml or 10,000 mIU/ml, antibody gold conjugate binds to the hCG antigen in the sample, and can not be further bind to the hCG antigen in the test area, thus produce no respective test line. When the hCG level in sample is below the respective detection limit, the unbound antibody gold conjugate will be bound to the hCG antigen at the test line, thus produce a visible test line.

If the hCG concentration in the sample is less than 25 mIU/ml, the test area of 25 mIU/ml, 100 mIU/ml and 500 mIU/ml are invisible, while the 200 mIU/ml and 10,000 mIU/ml test areas are visible. Control areas are always visible if the correct procedure is followed If the hCG concentration in the sample is higher than the respective detection limits of 25 mIU/ml, 500 mIU/ml and 1000 mIU/ml, the respective test areas of the test strips becomes visible, while the 200 mIU/ml and10,000 mIU/ml test areas are visible as long as the sample hCG concentration is less than 2000 mIU. Control areas are always visible if the correct procedure is followed.

If the hCG concentration in the sample is higher than 2000 mIU/ml but less than 10,000 mIU/ml, the respective 25 mIU/ml, 100 mIU/ml and 500 mIU/ml test areas of the test strips becomes visible, while the test area of 200 mIU/ml become invisible, and 10,000 mIU/ml test area is visible. Control areas are always visible if the correct procedure is followed.

If the hCG concentration in the sample is higher than 10,000 mIU/ml, the respective 25 mIU/ml, 100 mIU/ml and 500 mIU/ml test areas of the test strips becomes visible, while the test area of 2000 mIU/ml and 10,000 mIU/ml become invisible. Control areas are always visible if the correct procedure is followed.

FIG. 1 illustrates an example of a cassette 10 having a plurality of strips 12, 14, 16, 18, and 20 in accordance to an embodiment of the present invention. The plurality of strips are assembled in the cassette 10. Each strip 12, 14, 16, 18, and 20 includes a backing sub-strip, an absorbent material sub-strip tip, and a cover sub-strip having a clear portion window 22. The absorbent material sub-strip tip is attached to a glass fiber (or any absorbent material) which has anti-hCG antibody-Colloidal Gold Conjugate embedded in the glassing fiber. Beneath the clear portion window 22 of each strip includes a control band of capture antibody and a test band of anti-hCG antibody (25 mIU/ml, 100 mIU/ml and 500 mIU/ml) or hCG antigen (2000 mIU/ml and 10,000 mIU/ml). The glass fiber (or any absorbent material) with the antibody gold conjugate is held between the absorbent materials sub-strip tip and the cover sub-strip having the clear portion window 22. The sub-strips are laminated with a short portion of each sub-strip tip of the absorbent material exposed at a dipping end for wetting. The window may have a T and a C on its inner side indicating the locations of the test band and control band, respectively.

Figure 2:
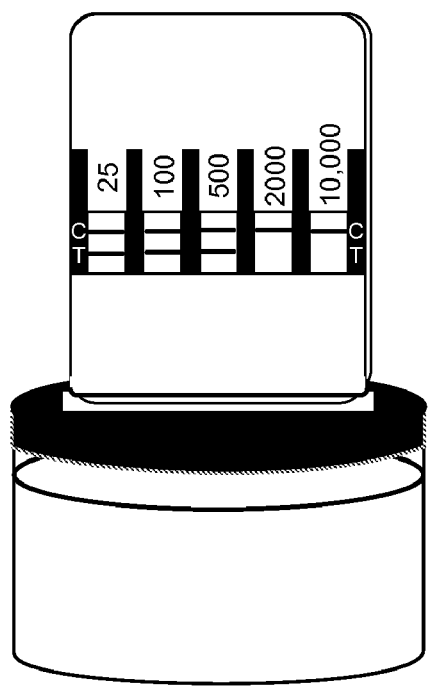
FIG. 2 illustrates a cassette being wetted by a urine sample.

FIG. 2 illustrates plurality of strips 12, 14, 16, 18, and 20 of the cassette being dipped into a fluid sample. The fluid sample is absorbed by the absorbent material which draws the fluid sample to the test bands and control bands of the plurality of strips.

Figure 3:
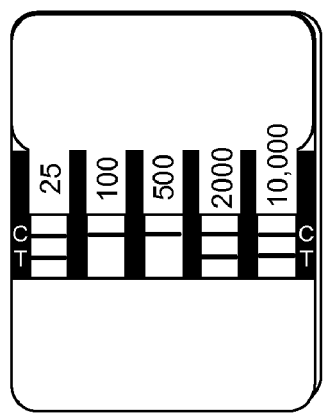
FIG. 3 illustrates the cassette indicating a positive result; i.e. the sample having hCG concentration greater than 25 mIU/ml but less than 100 mIU/ml.

FIG. 3 illustrates a cassette indicating a positive result of 25 mIU/ml. The 100 mIU/ml, and 500 mIU/ml test bands do not show color indicating that measured hCG is below 100 mIU/ml and 500 mIU/ml but greater than 25 mIU/ml. Since the 2,000 mIU/ml and 10,000 mIU/ml show test band color, the test band color indicates that measured hCG concentration is below 2,000 mIU/ml and 10,000 mIU/ml. Accordingly, the test cassette shows a 25 mIU/ml positive result. Note that the control band for the test strips show color which indicates a valid test.

Figure 4:
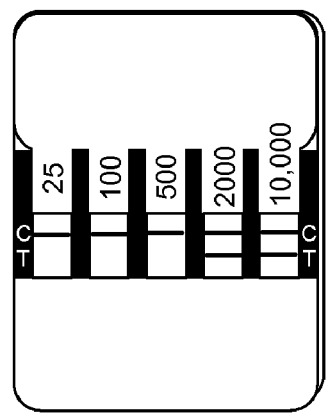
FIG. 4 illustrates the cassette indicating a negative result; i.e. the sample having hCG concentration less than 25 mIU/ml.

FIG. 4 illustrates a cassette indicating a negative result for measurable hCG. The 25 mIU/, 100 mIU/ml, and 500 mIU/ml test bands do not show color indicating that measured hCG is below 25 mIU/ml. The 2,000 mIU/ml and 10,000 mIU/ml show a test band color which indicates that measured hCG concentration is below 2,000 mIU/ml and 10,000 mIU/ml. Since the control band for the test strips show color indicating a valid test, the test cassette shows a hCG level of below 25 mIU/ml.

Figure 5:
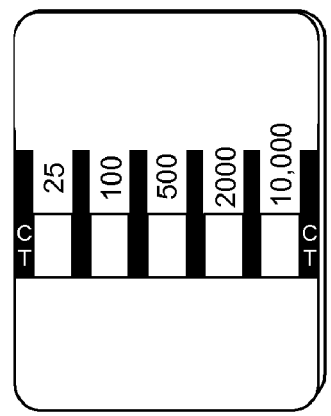
FIG. 5 illustrates the cassette indicating an invalid test.

FIG. 5 illustrates a cassette indicating an invalid test because the control band for the test strips does not show color.

Figure 6:
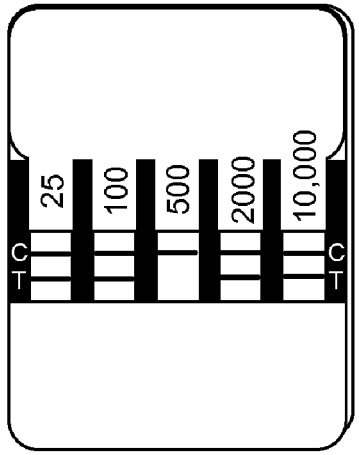
FIG. 6 illustrates the cassette indicating a positive result; i.e. the sample having hCG concentration greater than 100 mIU/ml, but less than 500 mIU/ml.

FIG. 6 illustrates a cassette indicating a 100 mIU/ml positive result. The 25 mIU/ml and 100 mIU/ml test bands do show color indicating that measured hCG is at least 100 mIU/ml but the 500 mIU/ml test band do not show color indicating that the measured hCG is below 500 mIU/ml. Since the 2,000 mIU/ml and 10,000 mIU/ml show test band color, the test band color indicates that measured hCG concentration is below 2,000 mIU/ml and 10,000 mIU/ml. Accordingly, the test cassette shows a 100 mIU/ml positive result. Note that the control band for the test strips show color which indicates a valid test.

Figure 7:
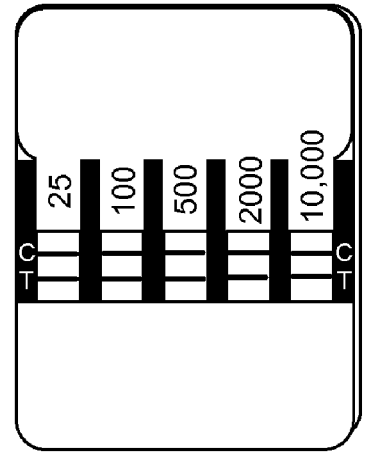
FIG. 7 illustrates the cassette indicating a positive result; i.e. the sample having hCG concentration greater than 500 mIU/ml but less than 2000 mIU/ml.

FIG. 7 illustrates a cassette indicating a 500 mIU/ml positive result. The 25 mIU/ml, 100 mIU/ml, and 500 mIU/ml test bands do show color indicating that measured hCG is at least 500 mIU/ml. The 2,000 mIU/ml and10,000 mIU/ml show test band color which indicates that measured hCG concentration is below 2,000 mIU/ml and 10,000 mIU/ml. Accordingly, the test cassette shows a 500 mIU/ml positive result. Note that the control band for the test strips show color which indicates a valid test.

Figure 8:
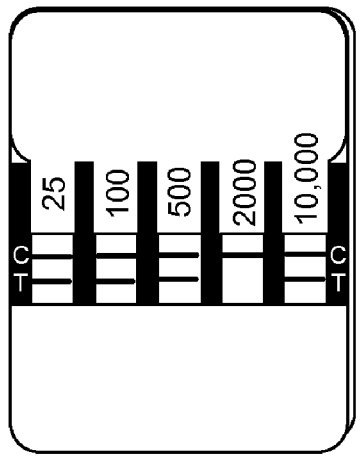
FIG. 8 illustrates the cassette indicating a positive result; i.e. the sample having hCG concentration greater than 2,000 mIU/ml but less than 10,000 mIU.

FIG. 8 illustrates a cassette indicating a 2,000 mIU/ml positive result. The 25 mIU/ml, 100 mIU/ml, and 500 mIU/ml test bands do show color indicating that measured hCG is at least 2,000 mIU/ml. The 2,000 mIU/ml does not show a test band color and the 10,000 mIU/ml show a test band color which indicates that measured hCG concentration is at least 2,000 mIU/ml and below 10,000 mIU/ml. Accordingly, the test cassette shows a 2,000 mIU/ml positive result. Note that the control band for the test strips show color which indicates a valid test.

Figure 9:
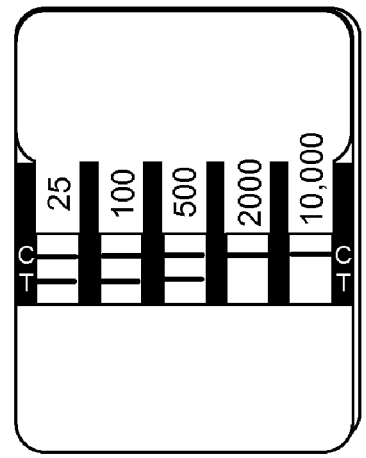
FIG. 9 illustrates the cassette indicating a positive result; i.e. the sample having hCG concentration greater than 10,000 mIU/ml.

FIG. 9 illustrates a cassette indicating a10,000 mIU/ml positive result. The 25 mIU/ml, 100 mIU/ml, and 500 mIU/ml test bands do show color indicating that measured hCG is at least 10,000 mIU/ml. The 2,000 mIU/ml and10,000 mIU/ml do not show test band color which indicates that measured hCG concentration is above 2,000 mIU/ml and 10,000 mIU/ml. Accordingly, the test cassette shows positive result with a hCG concentration of at least 10,000 mIU/ml. Note that the control band for the test strips show color which indicates a valid test.

The invention is to measure low to high hCG concentration levels typical to that of pre-pregnancy to varies stages of Gestational age.

Note that although a high range (2,000 mIU/ml and 10,000 IU/ml) and a low range (100 mIU/ml, 200 mIU/ml, and 500 mIU/ml) have been described here, it shall be understood that the specific sub-ranges can differ in the various embodiments. Furthermore, the high range may have high sub-ranges and can be referred to as a first high-subrange (e.g. 2000 mIU/ml), a second high-subrange (e.g. 10,000 mIU/ml), etc.; and the low range may have low sub-ranges and can be referred to as a first low-subrange(e.g. 100 mIU/ml), a second low-subrange(e.g. 200 mIU/ml), a third low-subrange (e.g. 500 mIU/ml), etc.

Further note that although a change in color has been described herein, indicators of any type can be used, and colors are not limited to any one particular color.

Urine, blood or other fluids maybe used as fluid samples.

While the invention has been described in details with reference to the present embodiment, it shall be appreciated that various changes and modifications are possible to those skilled in the art without departing the spirit of the invention. Thus, the scope of the invention is intent to be solely defined in the accompanying claims.

We claim:

1. A method for detection of the hCG concentration in a fluid sample using a plurality of test strips, wherein the test strips detects a hCG concentration range, wherein each of the test strips detects a distinct hCG concentration level within said hCG concentration range, wherein the distinct hCG concentration levels of the test strips are set at exponential levels within said hCG concentration range, and wherein each of the test strips provides an indicator when its respective hCG concentration level is detected, comprising the steps:
   contacting the test strips with the fluid sample;
   reacting the test strips with the fluid sample to detect the hCG concentration; and
   displaying by one or more of the reacted test strips the hCG concentration.

2. The method for detection of hCG concentration according to claim 1, wherein each of the test strips include an absorbent material having anti-hCG colloidal conjugate, a test band providing the indicator to indicate whether the respective hCG output concentration level for the respective test strip is met, and a control band providing a control indicator to indicate that the respective test strip is valid where the control band has antibodies capable of capturing conjugated color particles, wherein the reacting step includes substeps of:
   forming an antibody-antigen complex when hCG in the fluid sample binds with the colloidal conjugate;
   allowing the complex to migrate through said test strip via said test band and said control band;
   capturing said complex in the test band when the hCG concentration in the fluid sample is within the hCG concentration level of the respective test strip; and
   capturing said colloidal conjugate in the control band.

3. The method of detection of hCG concentration according to claim 2, wherein the capturing said complex step includes displaying the indicator of the respective test strip when the hCG concentration is equal to or greater than a predetermined first range and wherein the test band is coated with hcg-antibody.

4. The method of detection of hCG concentration according to claim 2, wherein the capturing said complex step includes displaying the indicator of the respective test strip when the hCG concentration is equal to or greater than a predetermined second range and wherein the test band is coated with hcg-antigen.

5. The method of detection of hCG concentration according to claim 3, wherein the capturing said complex step includes displaying the indicator of the respective test strip when the hCG concentration is equal to or greater than a predetermined second range and wherein the test band is coated with hcg-antigen.

6. The method of detection of hCG concentration according to claim 2, wherein the capturing said complex step includes displaying the indicator of the respective test strip for detecting hCG concentrations in the respective first or second range when the hCG concentration in the fluid sample is within the respective hCG concentration level in the respective range of the respective test stripes.

7. The method of detection of hCG concentration according to claim 2, wherein the capturing said complex step includes displaying the indicator of the respective test strip a first selected color when the hCG concentration is equal to or greater than a first range.

8. The method of detection of hCG concentration according to claim 2, wherein the capturing said complex step includes displaying the indicator of the respective test strip a second selected color when the hCG concentration is equal to or greater than a second range.

9. The method of detection of hCG concentration according to claim 7, wherein the capturing said complex step includes displaying the indicator of the respective test strip a second selected color when the hCG concentration is equal to or greater than a second range.

10. The method for detection of hCG concentration according to claim 2, wherein the test strips include an absorbent material having anti-hCG colloidal conjugate, a test band with anti-hCG antigen, and a control band with antibody capable of capture conjugated color particles, wherein the reacting step includes the substeps of:
    forming an antibody-antigen complex when hCG in the fluid sample binds with the colloidal conjugate;
    producing no change in the test band when the hCG concentration is at or exceed a predetermined hCG concentration; and
    displaying the control band color as the conjugated complex binds with the capture antibody.

11. The method of detection of hCG concentration according to claim 10, wherein the capturing said complex includes displaying the indicator of the respective test strip when the hCG concentration is equal to or greater than a predetermined first range.

12. The method of detection of hCG concentration according to claim 10, wherein the capturing said complex step includes displaying the indicator of the respective test strip when the hCG concentration is equal to or greater than a predetermined second range.

13. The method of detection of hCG concentration according to claim 11, wherein the capturing said complex step includes displaying the indicator of the respective test strip when the hCG concentration is equal to or greater than a predetermined second range.

14. The method of detection of hCG concentration according to claim 10, wherein the capturing said complex step includes displaying the indicator of the respective test strip for detecting hCG concentrations in the respective first or second range when the hCG concentration in the fluid sample is within the respective hCG concentration level in the respective range of the respective test stripes.

15. The method of detection of hCG concentration according to claim 10, wherein the capturing said complex step includes displaying the indicator of the respective test strip a first selected color when the hCG concentration is equal to or greater than a first range.

16. The method of detection of hCG concentration according to claim 10, wherein the capturing said complex step includes displaying the indicator of the respective test strip a second selected color when the hCG concentration is equal to or greater than a second range.

17. The method of detection of hCG concentration according to claim 15, wherein the capturing said complex step includes displaying the indicator of the respective test strip a second selected color when the hCG concentration is equal to or greater than a second range.

* * * * *